(12) United States Patent
Manzo

(10) Patent No.: US 8,328,866 B2
(45) Date of Patent: *Dec. 11, 2012

(54) METHOD AND APPARATUS FOR RADICAL PROSTATECTOMY ANASTOMOSIS INCLUDING AN ANCHOR FOR ENGAGING A BODY VESSEL AND DEPLOYABLE SUTURES

(75) Inventor: Scott E. Manzo, Shelton, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/187,080

(22) Filed: Jul. 20, 2011

(65) Prior Publication Data

US 2011/0276068 A1 Nov. 10, 2011

Related U.S. Application Data

(60) Continuation of application No. 12/618,974, filed on Nov. 16, 2009, now Pat. No. 8,002,819, which is a division of application No. 10/550,705, filed as application No. PCT/US03/11914 on Apr. 16, 2003, now Pat. No. 7,621,924.

(51) Int. Cl.
*A61B 17/08* (2006.01)
(52) U.S. Cl. ...................................................... 623/1.23
(58) Field of Classification Search .................. None
See application file for complete search history.

(56) References Cited

U.S. PATENT DOCUMENTS

| | | | |
|---|---|---|---|
| 4,553,543 A | 11/1985 | Amarasinghe | |
| 5,322,501 A | 6/1994 | Mahmud-Durrani | |
| 5,387,235 A | 2/1995 | Chuter | |
| 5,496,332 A | 3/1996 | Sierra et al. | |
| 5,545,171 A | 8/1996 | Sharkey et al. | |
| 5,836,955 A * | 11/1998 | Buelna et al. | 606/148 |
| 5,954,732 A * | 9/1999 | Hart et al. | 606/144 |
| 6,451,034 B1 | 9/2002 | Gifford et al. | |
| 6,562,052 B2 * | 5/2003 | Nobles et al. | 606/144 |
| 6,899,718 B2 | 5/2005 | Gifford et al. | |
| 6,923,820 B1 | 8/2005 | Nash et al. | |
| 2002/0045908 A1 * | 4/2002 | Nobles et al. | 606/144 |
| 2004/0050393 A1 | 3/2004 | Golden et al. | |
| 2004/0068276 A1 | 4/2004 | Golden et al. | |
| 2005/0277981 A1 * | 12/2005 | Maahs et al. | 606/213 |
| 2007/0106313 A1 | 5/2007 | Golden et al. | |
| 2007/0213750 A1 | 9/2007 | Weadock | |

OTHER PUBLICATIONS

International Search Report for PCT/US03/11914 date of Mailing Dec. 18, 2003 (2 pages).

* cited by examiner

*Primary Examiner* — Melanie Tyson
*Assistant Examiner* — Son Dang

(57) ABSTRACT

A device for joining a first body vessel to a second body vessel including a cartridge having a distal end and defining a longitudinal axis, a radially expandable anchor disposed at the distal end of the cartridge for engaging the first body vessel, the expandable anchor having an initial condition and an expanded condition wherein the expandable anchor is radially larger than the expandable anchor in the initial condition, and a plurality of sutures disposed within the cartridge and being deployable therefrom so as to engage the second body vessel, the sutures being threaded through the expandable anchor.

8 Claims, 11 Drawing Sheets

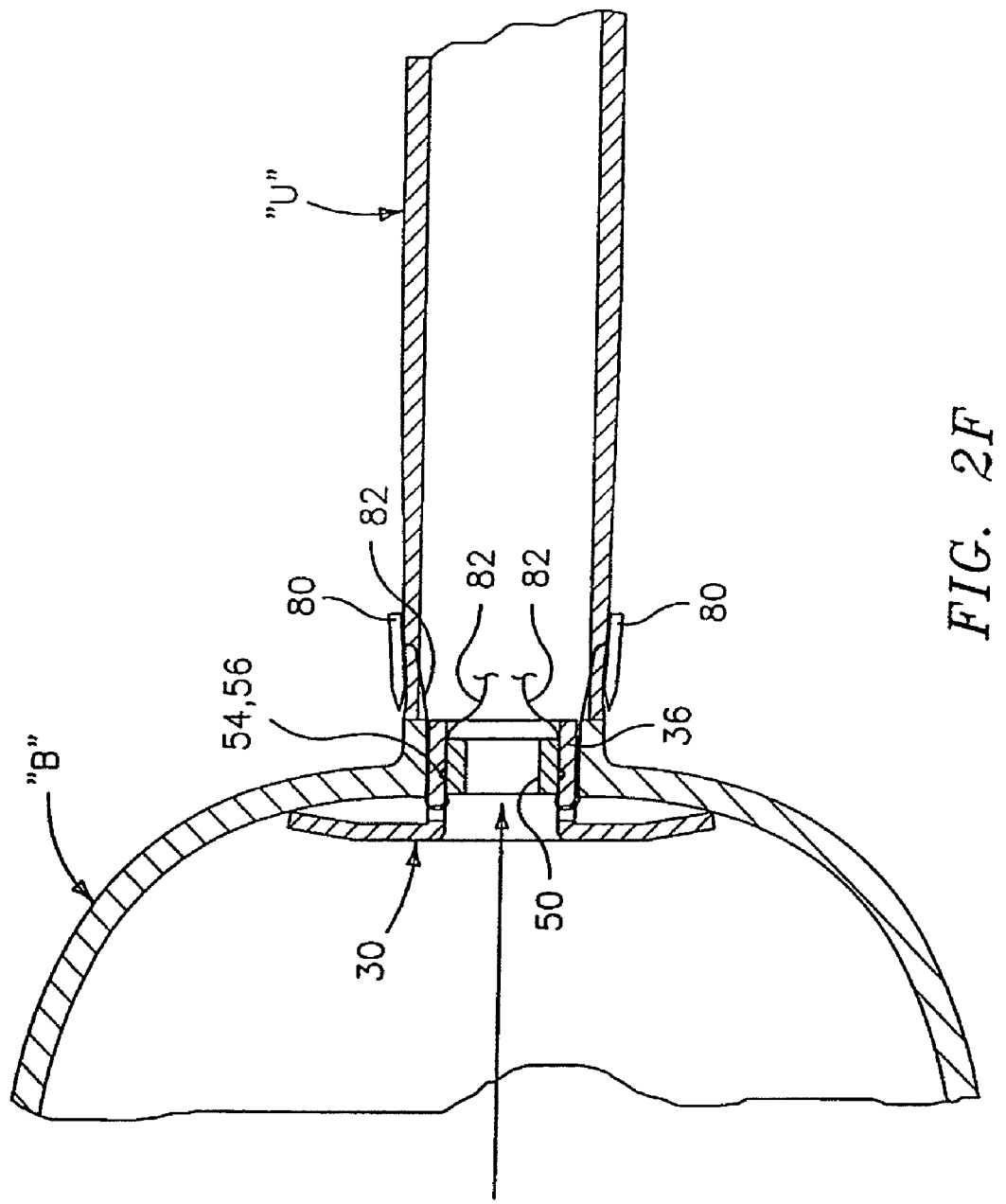

METHOD AND APPARATUS FOR RADICAL PROSTATECTOMY ANASTOMOSIS INCLUDING AN ANCHOR FOR ENGAGING A BODY VESSEL AND DEPLOYABLE SUTURES

CROSS-REFERENCE TO RELATED APPLICATIONS

This application is a Continuation of U.S. application Ser. No. 12/618,974 filed Nov. 16, 2009 now U.S. Pat. No. 8,002,819 which is a Divisional Application claiming the benefit of and priority to U.S. application Ser. No. 10/550,705 filed Sep. 27, 2005, now U.S. Pat. No. 7,621,924 which is a U.S. National Phase filing under 35 USC §371 of International Application Serial No. PCT/US03/11914, filed Apr. 16, 2003, the entire contents of which are hereby incorporated by reference in their entirety.

BACKGROUND

1. Technical Field

The present disclosure relates an apparatus and methods for anastomosing two hollow body parts and, more particularly to apparatus and methods for anastomosing a urethral stump of a patient to the bladder following a radical prostatectomy.

2. Background of Related Art

Most body conduits are generally cylindrical in configuration and have a circular cross-section. When it is desired to suture such a conduit, typically for attachment to another body conduit, sutures are placed around the circumference of the conduit in order to maintain the patency of its lumen or channel. This type of attachment is commonly referred to as an anastomosis. It can be appreciated that the sutures made on top of the conduit (i.e., on the side facing the surgeon) in an anastomosis are made relatively more easily than the sutures made underneath the conduit (i.e., on the side facing away from the surgeon).

The complexity of anastomosis attachment is made manifestly apparent in a surgical procedure referred to generally as a radical prostatectomy (i.e., a well established surgical procedure for patients with localized prostatic carcinoma). In general, radical prostatectomy procedures require the removal of cancerous tissue while preserving sexual function and continence in the patient. There are two primary types of radical prostatectomy approaches for the removal of prostate cancer, the retropubic approach and the perineal approach.

In the retropubic approach, a long up-and-down incision is made in the midline of the abdomen from the navel to the pubic bone. After the lymph nodes have been removed for study by the pathologist and a determination has been made to proceed with the removal of the prostate gland, the space underneath the pubic bone is cleaned and dissected and the removal of the entire prostate gland is generally begun at the end that is farthest from the bladder, i.e., next to the external urethral sphincter. Next, the prostatic urethra is divided, the prostatic urethra and the prostate gland through which it goes are then pulled upwards toward the bladder while the dissection continues behind the prostate gland, separating it from the layer of tissue that is connected to the rectum on its other side. As the dissection continues between the prostate and the rectum, the seminal vesicles, which are behind the base of the bladder will be removed along with the prostate gland. Once the seminal vesicles are free, the entire prostate gland and the seminal vesicles are removed. The bladder neck is then stitched closed to a small enough diameter so that it is about the same size as the stump of the urethra from which the prostate was detached. The bladder neck is then pulled down into the pelvis and positioned against the urethral stump and stitched thereto. This stitching is done typically around a Foley catheter which has been inserted through the penis all the way into the bladder.

In the perineal approach, an inverted "U" shaped incision is made going right over the anus, with the center of the "U" about three centimeters above the margin of the anus. The prostate gland is then freed from its surrounding structures by gentle dissection, and the urethra at the end of the prostate farthest from the bladder is isolated and divided. The bladder neck is freed from the prostate, and, once the prostate gland has been removed and the bladder neck has been closed sufficiently so that the size of its opening approximates the size of the urethral opening, the urethra and the bladder neck are stitched together. Once again, a Foley catheter is left in place postoperatively for about two weeks.

In each of the above described procedures, it is the attachment of the urethral stump to the bladder neck which is particularly difficult and complex. This difficulty is complicated by the tendency of the urethral stump to retract into adjacent tissue. As a result, considerable time and effort must be expended to re-expose the urethral stump and begin the re-anastomosis procedure. Further complicating this procedure is the fact that the urethral stump is hidden beneath the pubic bone thus requiring that the surgeon work at a difficult angle and in positions that are uncomfortable and limiting.

Various devices have been proposed for facilitating this procedure. In U.S. Pat. No. 5,591,179, issued to Edelstein, there is disclosed a suturing device including a shaft with portions defining an interior channel extending between a proximal and a distal end of the shaft. This channel includes a generally axial lumen which extends to the proximal end of the shaft and a generally transverse lumen which extends from the axial lumen distally outwardly to an exit hole at the outer surface of the shaft. A needle and suture can be back loaded into the transverse lumen of the channel while a generally non-compressible member can be movably mounted in the axial lumen of the channel. At the proximal end of the shaft a handle is provided with means operative to push the member distally through the lumen to deploy or expel the needle.

In U.S. Pat. No. 4,911,164, issued to Roth, there is disclosed a suture guide with a curved distal portion. The distal portion of the suture guide has a plurality of exterior axial grooves which can be used to align and guide a curved needle and attached suture. In order to drive the urethral stump to an accessible position, the device is provided with a plurality of outwardly extendable members which engage the lumen of the urethra. These members make it possible to push the urethral stump into approximation with the bladder neck.

In U.S. Pat. No. 5,047,039, issued to Avant et al., there is disclosed a surgical device for the ligation of a dorsal vein and subsequent anastomosis. This device contains a pair of enclosed needles each having an attached suture which needles may be driven from the shaft of the device into adjacent tissue.

In general, none of the devices disclosed in the prior art references above is simple to use or makes the anastomosis of the urethral stump to the bladder neck easier. As such, each surgical procedure using the prior art devices continues to be time consuming and to require great skill. In addition, these prior art references do not disclose a suture device which can accurately position a plurality of anchor and suture combinations, for use at or near the severed end of a body conduit, simultaneously. Accordingly, the need exists for radical prostatectomy anastomosis devices which overcome the drawbacks of the prior art devices and which are quick and simple to use.

SUMMARY

Devices and methods for performing a surgical anastomotic procedure are disclosed herein.

According to one aspect of the present disclosure, a device for joining a first body vessel to a second body vessel is provided including a cartridge having a distal end and defining a longitudinal axis, a radially expandable anchor disposed at the distal end of the cartridge for engaging the first body vessel, the expandable anchor having an initial condition and an expanded condition wherein the expandable anchor is radially larger than the expandable anchor in the initial condition, and a plurality of sutures disposed within the cartridge and being deployable therefrom so as to engage the second body vessel, the sutures being threaded through the expandable anchor.

The expandable anchor includes a plurality of flexible arms biased in an expanded position. The cartridge includes an inner member and an outer member having a lumen dimensioned to receive the inner member, the sutures being disposed in channels formed in the inner member.

The anchor has a central passage and the sutures extend through the expandable anchor and proximally through the central passage. The expandable anchor is disposed between the inner member and the outer member. The sutures desirably have distal ends and needle anchors attached to the distal ends, the needle ends being deployable from the cartridge.

It is envisioned that the device further includes a ring disposed within the outer member for securing the sutures to the expandable anchor. The expandable anchor desirably includes a plurality of holes, each of the holes receiving one of the sutures. The expandable anchor includes a plurality of arms connected by members.

The inner member desirably includes a ring having connection features for engaging the arms. It is envisioned that the ring, expandable anchor and members are sized so that when the ring engages the arms, the members are broken and the arms remain attached to the ring. The inner member has a tapered distal end.

According to another aspect of the present disclosure, a device for joining a first body vessel to a second body vessel is provided and includes a cartridge having a distal end and defining a longitudinal axis, an anchor disposed at the distal end of the cartridge for engaging the first body vessel, and a plurality of sutures disposed within the cartridge and being deployable therefrom so as to engage the second body vessel, the sutures being threaded through the anchor.

The anchor includes a plurality of outwardly extending arms. The cartridge includes an inner member and an outer member having a lumen dimensioned to receive the inner member, the sutures being disposed in channels formed in the inner member. The outer member and anchor are sized so that the anchor is disposed along the longitudinal axis within the outer member. The anchor has a central passage and the sutures extend through the anchor and proximally through the central passage. The sutures have distal ends and needle anchors attached to the distal ends, the needles being deployable from the cartridge.

The device further includes a ring disposed within the outer member for securing the sutures to the expandable anchor.

The anchor includes a plurality of holes, each of the holes receiving one of the sutures.

According to a still further aspect of the present disclosure, an apparatus for performing a surgical anastomosis is provided and includes a sleeve having a proximal and a distal end and defining a longitudinal axis and a tubular body configured and adapted to be slidably received within the sleeve, the tubular body defining a central lumen extending longitudinally therethrough.

The apparatus further includes a firing head operatively coupled to a distal end of the tubular body. The firing head has a recess co-axially aligned and interconnected with the central lumen of the tubular body. The firing head further includes at least one needle passage formed therein and extending into the central lumen of the tubular body.

The apparatus includes an anchor configured and adapted to be received within the distal end of the sleeve. The anchor has a hub, a plurality of resilient arms extending from the hub and an annular flange extending from a proximal surface of the hub. Each of the plurality of arms has a first position in axial alignment with the longitudinal axis of the sleeve and a second position orthogonal to the longitudinal axis of the sleeve. The anchor further includes a central passage extending through the hub and the annular flange.

The apparatus further includes a needle pusher assembly having at least one push rod slidably received within a respective needle passage. A lock collar is provided which is configured and adapted to be tightly fit in the central passage of the anchor. The lock collar is held within the recess of the firing head by at least one break-away tab extending from an outer surface of the lock collar to an inner surface of the recess of the firing head.

The apparatus includes at least one needle anchor having a suture secured thereto. The at least one needle anchor is slidably received in a respective needle passage. The suture runs from the at least one needle anchor, out a respective needle passage, into the central passage of the anchor through a respective hole formed in the flange, proximally into the recess of the firing head, between the lock collar and the firing head and proximally through the central lumen of the tubular body.

A method of performing a surgical anastomotic procedure, using the apparatus disclosed above is provided and includes providing apparatus as disclosed above, loading the distal end of the sleeve with the anchor such that each of the plurality of arms of the anchor are in the first position, passing the apparatus through a body lumen until the anchor is positioned entirely within a body vessel, deploying the anchor by withdrawing the sleeve proximally so that the arms are in the second position, withdrawing the sleeve and tubular body proximally through the body lumen until the needle passages are within the body lumen, firing the needle anchors through the body lumen by driving the push rods of the pusher assembly distally through the central lumen of the tubular body, approximating the body vessel to the body lumen by pulling on the at least one suture, holding the at least one suture in place, advancing the tubular body through the body lumen and fitting the lock collar into the flange of the anchor to thereby fix the at least one suture in place.

The method further includes the steps of removing the prostate gland, freeing the urethra from the prostate gland to thereby define a urethral stump, and freeing the prostate gland from the bladder to define a bladder neck, The presently disclosed anastomosis devices and apparatus, together with attendant advantages, will be best understood by reference to the following detailed description in conjunction with the figures below.

BRIEF DESCRIPTION OF THE DRAWINGS

The accompanying drawings, which are incorporated in and constitute a part of this specification, illustrate embodiments of the disclosure and, together with the general description given above, and the detailed description of the embodiments given below, serve to explain the principles of the present disclosure.

FIG. 2F is a cross-sectional side elevational view of the apparatus as shown in FIG. 1B, following the surgical procedure, with the sleeve and the tubular body removed from the operative site;

DETAILED DESCRIPTION OF PREFERRED EMBODIMENTS

Figure 1A:
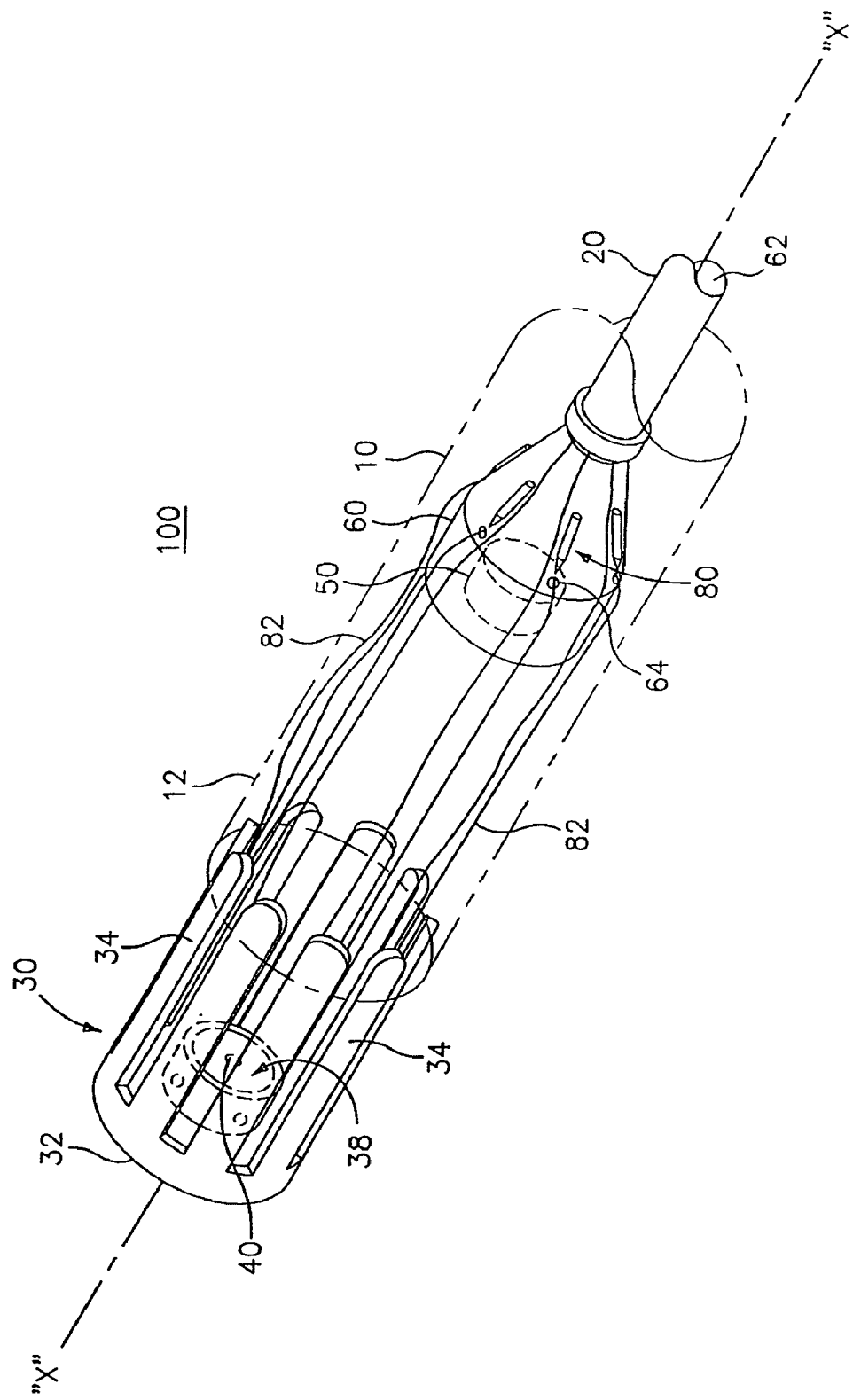
FIG. 1A is a perspective view of an embodiment of a distal end view of an anastomosis apparatus, in accordance with the present disclosure, shown in an insertion position.

Preferred embodiments of the presently disclosed apparatus for performing an anastomosis will now be described in detail with reference to the drawing figures wherein like reference numerals identify similar or identical elements. In the drawings and in the description which follows, the term "proximal", as is traditional will refer to the end of the surgical device or instrument of the present disclosure which is closest to the operator, while the term "distal" will refer to the end of the device or instrument which is furthest from the operator.

Figure 1B:
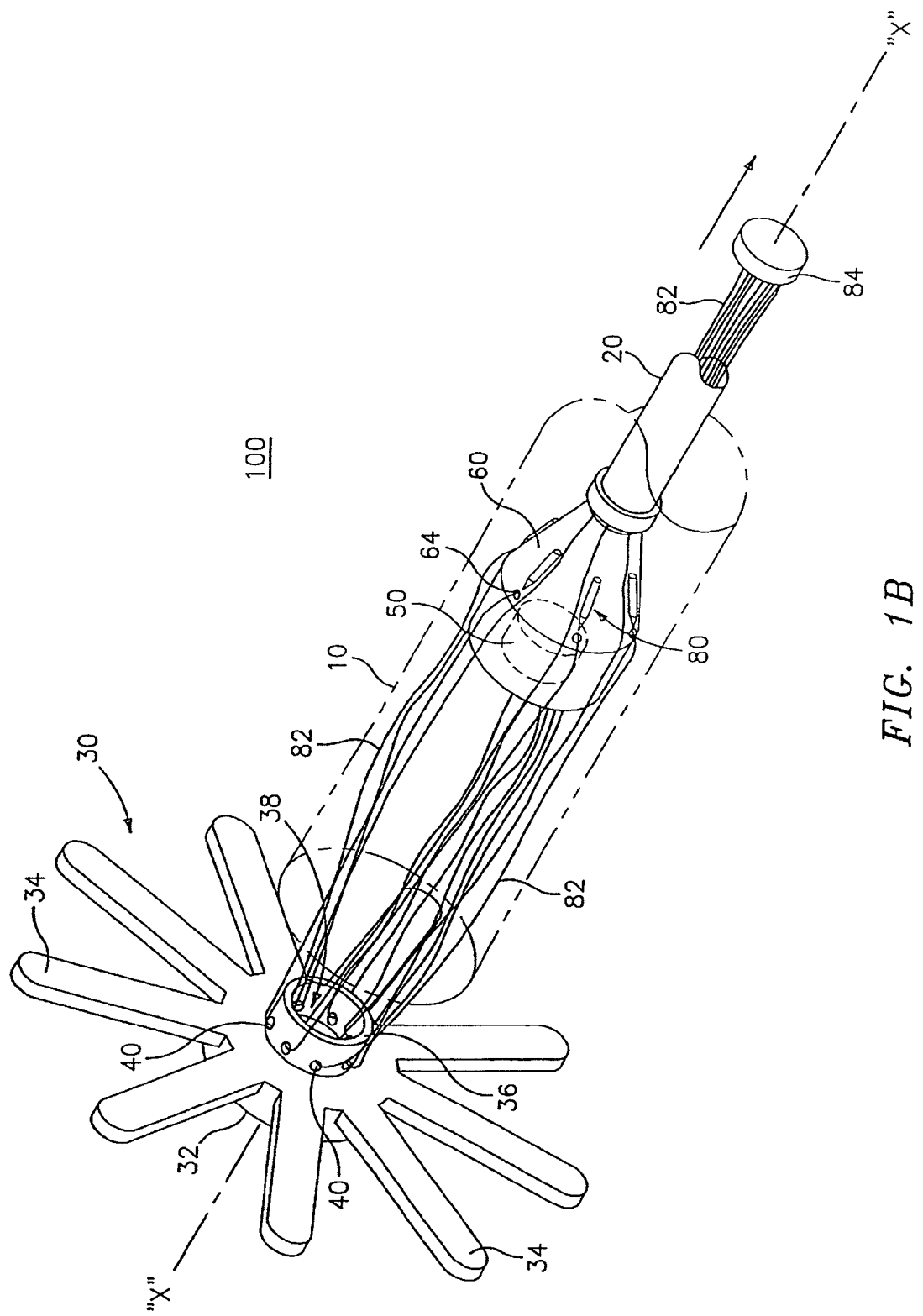
FIG. 1B is a perspective view of the apparatus of FIG. 1, shown in a deployed position.

Referring to FIGS. 1A to 2F, and in particular to FIGS. 1A and 1B, an anastomosis apparatus in accordance with the present disclosure, is shown generally as reference numeral 100. Although apparatus 100 offers significant advantages to a radical prostatectomy procedure, it will be understood that the device is applicable for use in any anastomotic procedure where two body vessels are to be secured to one another, such as where the end of a conduit is to be sutured or otherwise secured to a hollow body organ.

As seen in FIGS. 1A and 1B, apparatus 100 includes a sleeve 10 (in phantom), a tubular body 20 slidably received within sleeve 10 and an expandable anchor 30 received within a distal end 12 of sleeve 10. Sleeve 10 defines a central longitudinal axis "X".

Expandable anchor 30 includes a hub 32, a plurality of resilient arms 34 extending radially from hub 32 and an annular flange 36 extending from a proximal surface of hub 32. Hub 32 and flange 36 define a central passage 38 extending completely therethrough. Flange 36 includes a plurality of holes 40 formed radially therethrough. Preferably, hub 32 has a radius which is less than the radius of sleeve 10. In addition, annular flange 36 has a radius which is less than the radius of hub 32.

In accordance with the present disclosure, arms 34 can be biased from a first radially extended orientation, as seen in FIG. 1B, to a second deflected orientation, as seen in FIG. 1A, wherein arms 34 are axially aligned with the longitudinal "X" axis and do not extend beyond the radius of sleeve 10. While arms 34 have been shown as generally rectangular in shape, it is envisioned that arms 34 may assume other configurations including, but not limited to, circular, triangular, etc.

Tubular body 20 includes a needle firing head 60 operatively coupled to a distal end thereof and a central lumen 62 extending completely through tubular body 20 and firing head 60. A plurality of radially oriented needle passages 64 are formed in firing head 60 and extend into central lumen 62. Preferably, needle passages 64 are oriented in a distal direction.

Figure 2A:
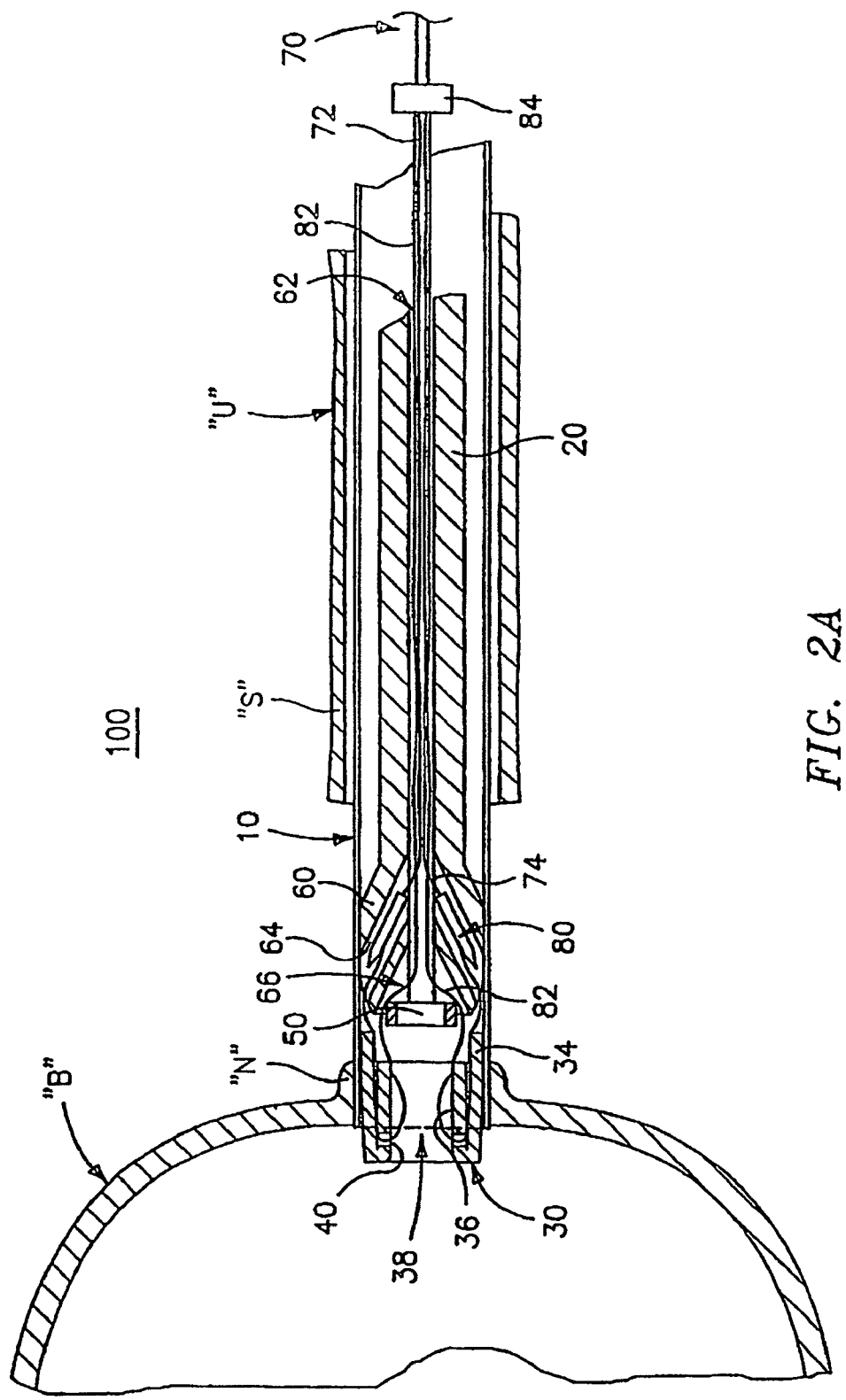
FIG. 2A is a cross-sectional side elevational view showing the apparatus according to the present disclosure as shown in FIG. 1A, inserted through a body lumen and into a hollow body organ.

Firing head 60 further includes a recess 66 co-axially formed in a proximal end thereof (see FIG. 2A). Recess 66 of firing head 60 is configured and adapted to retain a lock collar 50 therein. Preferably, lock collar 50 has an external radius which is slightly smaller than an internal radius of flange 36 of anchor expandable anchor 30. In this manner, lock collar 50 tightly fits into flange 36, thereby creating a friction fit type coupling. Recess 66 of firing head 60 has an internal radius which is larger than the external radius of lock collar 50. Lock collar 50 can be provided with an annular rim 54 (see FIG. 2C) formed along the outer surface thereof. It is envisioned that annular rim 54 is to be received in and mate with an annular channel 56 (see FIG. 2C) formed in the inner surface of flange 36. In this manner, in addition to the friction fit type coupling, when lock collar 50 is received in flange 36, annular rim 54 snaps into annular channel 56, thereby further securing lock collar 50 in flange 36 thereby also providing the user with a tactile feel as to when lock collar 50 is properly and fully received within flange 36.

Figure 2B:
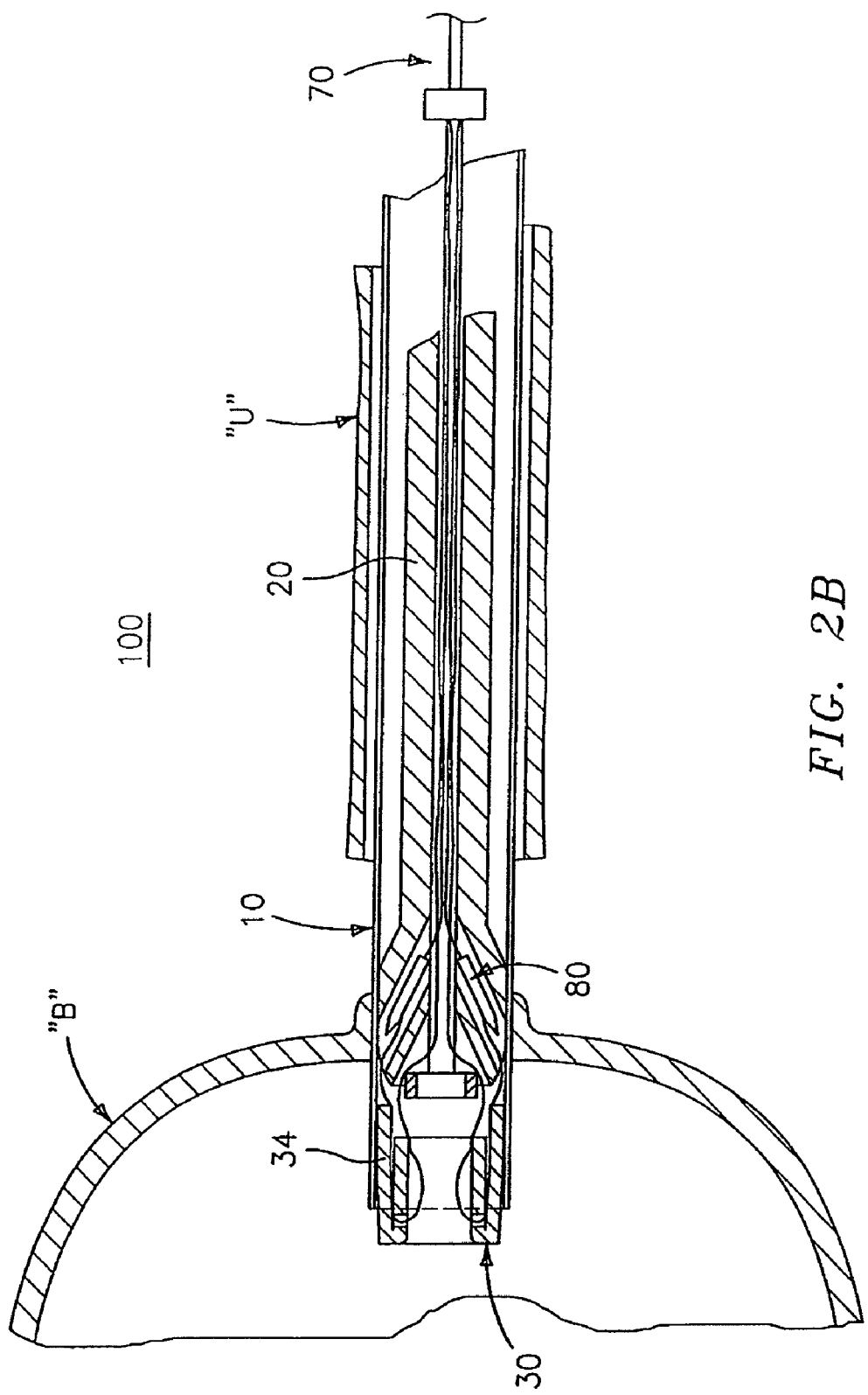
FIG. 2B is a cross-sectional side elevational view showing the apparatus according to the present disclosure as shown in FIG. 1A, inserted through a body lumen and further into a hollow body organ.
Figure 2C:
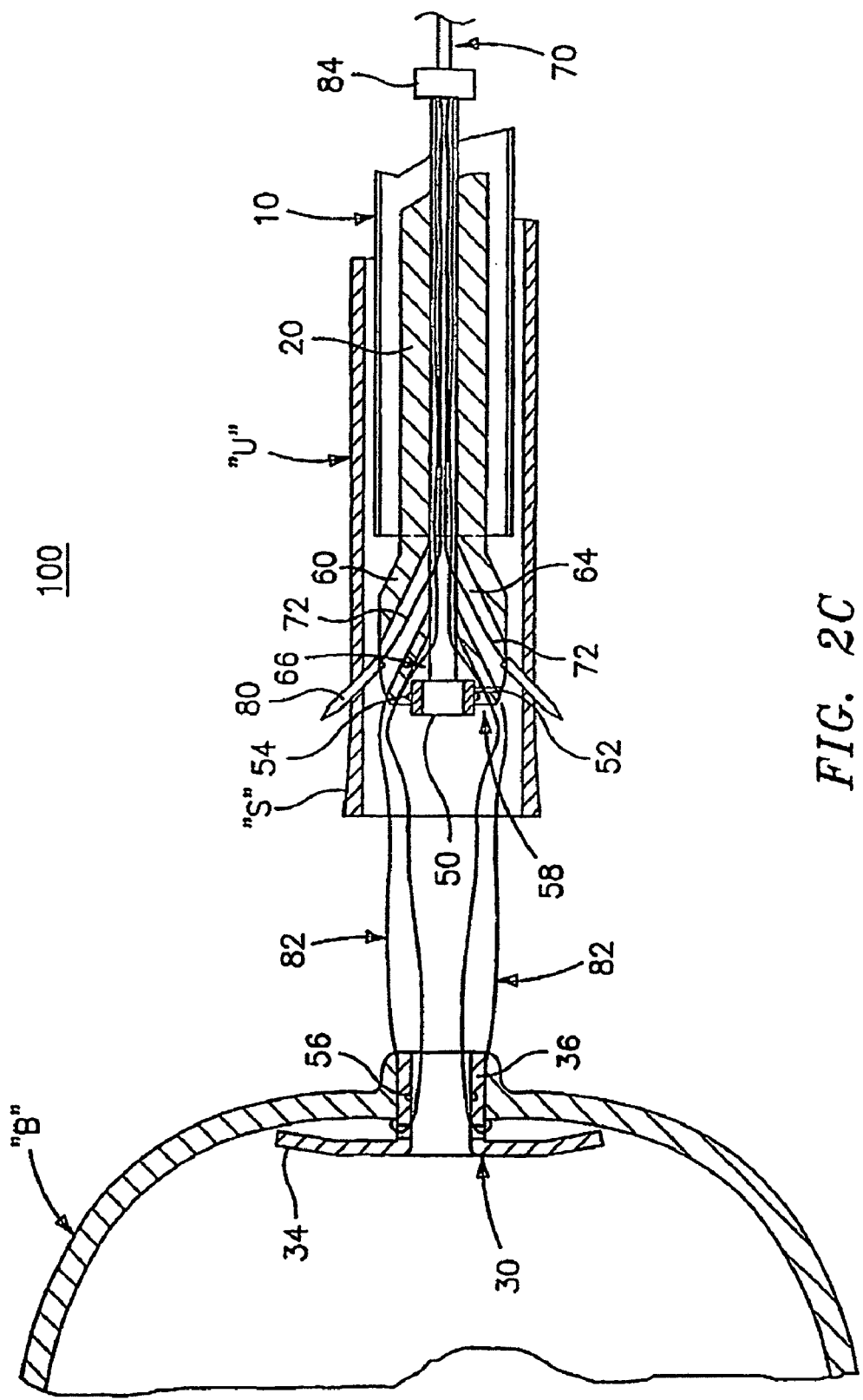
FIG. 2C is a cross-sectional side elevational view of the apparatus as shown in FIG. 1B, with an expandable anchor in accordance with the present disclosure, deployed within the hollow body organ and needle anchors being fired into the body lumen.

It is envisioned that lock collar 50 is retained in recess 66 by a plurality of break-away tabs 52 which interconnect lock collar 50 and firing head 60 (see FIG. 2C). The internal radius of recess 66 is selected such that lock collar 50 is centrally suspended therein by break-away tabs 52 thereby defining a plurality of passages 58 (see FIG. 2C) between lock collar 50 and recess 66.

In accordance with the present disclosure, apparatus 100 further includes a needle pusher assembly 70 (see FIG. 2A). Pusher assembly 70 includes a plurality of push rods 72 operatively coupled to one another at a proximal end thereof and slidably disposed within central lumen 62 of tubular body 20. Push rods 72 have a distal end 74 which is oriented to be received within needle passages 64. Preferably, pusher assembly 70 includes a push rod 72 for each needle passage 64. It is envisioned that push rods 72 are made from a resilient material in order to permit deflection of push rods 72 and have sufficient rigidity in order to resist compressive forces acting thereon. In accordance with the present disclosure, as pusher assembly 70 is advanced distally through central lumen 62, push rods 72 slide through a respective needle passage 64.

Push rods 72 may be arranged as disclosed in commonly assigned U.S. patent application entitled "Method and apparatus for Radical Prostatectomy Anastomosis Including an Anchor for Engaging a Body Vessel and Deployable Sutures", invented by Scott Manzo and filed on an even date herewith, the disclosure of which is hereby incorporated by reference herein in its entirety.

Apparatus 100 further includes a plurality of needle anchors 80 slidably received within needle passages 64. Each needle anchor 80 is provided with a suture 82 having a first end preferably affixed to a mid-point of a respective needle anchor 80 and a second end affixed to a common handle 84. In accordance with the present disclosure, each suture 82 runs from a respective needle anchor 80, distally out of a respective needle passage 64, into central passage 38 of flange 36 through a respective hole 40, proximally into recess 66 of firing head 60, through passages 58 between lock collar 50 and firing head 60 and proximally through central lumen 62 of tubular body 20 to handle 84.

Preferably, expandable anchor 30, lock collar 50, needle anchors 80 and sutures 82 are made from a medical grade bio-absorbable material, such as, for example, polyglycolic acid (PGA) and/or polylactic acid (PLA). It is envisioned that expandable anchor 30, lock collar 50, needle anchors 80 and sutures 82 have sufficient endurance to retain their structural integrity for at least the period required for a natural growth joining of tissue portions for a given anastomotic procedure.

A preferred method of use and operation of anastomosis apparatus 100 in performing a radical prostatectomy anastomosis will now be described in greater detail with reference to FIGS. 1A-2F and in particular with reference to FIGS. 2A-2F. Apparatus 100 can be used in either the retropubic or the perineal prostatectomy approaches. With the prostate removed, the bladder neck "N" of the bladder "B" is first reconstructed by everting the inner mucosal lining of bladder "B" and suturing it down to the outer wall of bladder "B", using known surgical techniques. Likewise, urethral stump "S" of urethra "U" is reconstructed by everting the inner mucosal lining of urethral stump "S" and suturing it down to the outer wall of urethra "U", using known surgical techniques.

Preferably, with bladder neck "N" reconstructed, bladder neck "N" is sized to properly accommodate expandable anchor 30 within bladder "B" using a standard tennis racket type closure (i.e., the opening of the bladder neck constituting the head of the tennis racket and a radial incision extending from the bladder neck constituting the handle portion of the tennis racket). Most preferably, bladder neck "N" is sized to be approximately 7-8 mm in diameter.

With bladder neck "N" reconstructed, apparatus 100 is passed trans-urethrally through urethra "U" until the distal end of sleeve 10 extends out of urethra "U" and into bladder "B", as seen in FIG. 2A. In particular, as seen in FIG. 2B, apparatus 100 is positioned such that biased arms 34 of expandable anchor 30 are located entirely within bladder "B". With apparatus 100 so positioned, sleeve 10 is withdrawn proximally while tubular body 20 is maintained stationary. Accordingly, as sleeve 10 passes the ends of arms 34, arms 34 are automatically biased to the radially extended orientation, as seen in FIG. 2C.

With continued reference to FIG. 2C, sleeve 10 and tubular body 20 are then withdrawn proximally into urethra "U" until needle passages 64 are within urethra "U". Sleeve 10 is then withdrawn proximally until needle passages 64 are exposed. With needle passages 64 exposed, needle pusher assembly 70 is advanced distally through tubular body 20. As such, the distal ends of push rods 72 abut against needle anchors 80 thereby forcing needle anchors 80 through urethral stump "S". Pusher assembly 70 is advanced distally until push rods 72 push needle anchors 80 completely through urethral stump "S". Preferably, each needle anchor 80 includes a pointed tip which aides in the penetration of needle anchors 80 into urethral stump "S". Following the anchoring of needle anchors 80 to urethral stump "S", pusher assembly 70 is withdrawn proximally into tubular body 20 at least until the distal ends of each push rod 72 is within tubular body 20 (see FIG. 2D).

Figure 2D:
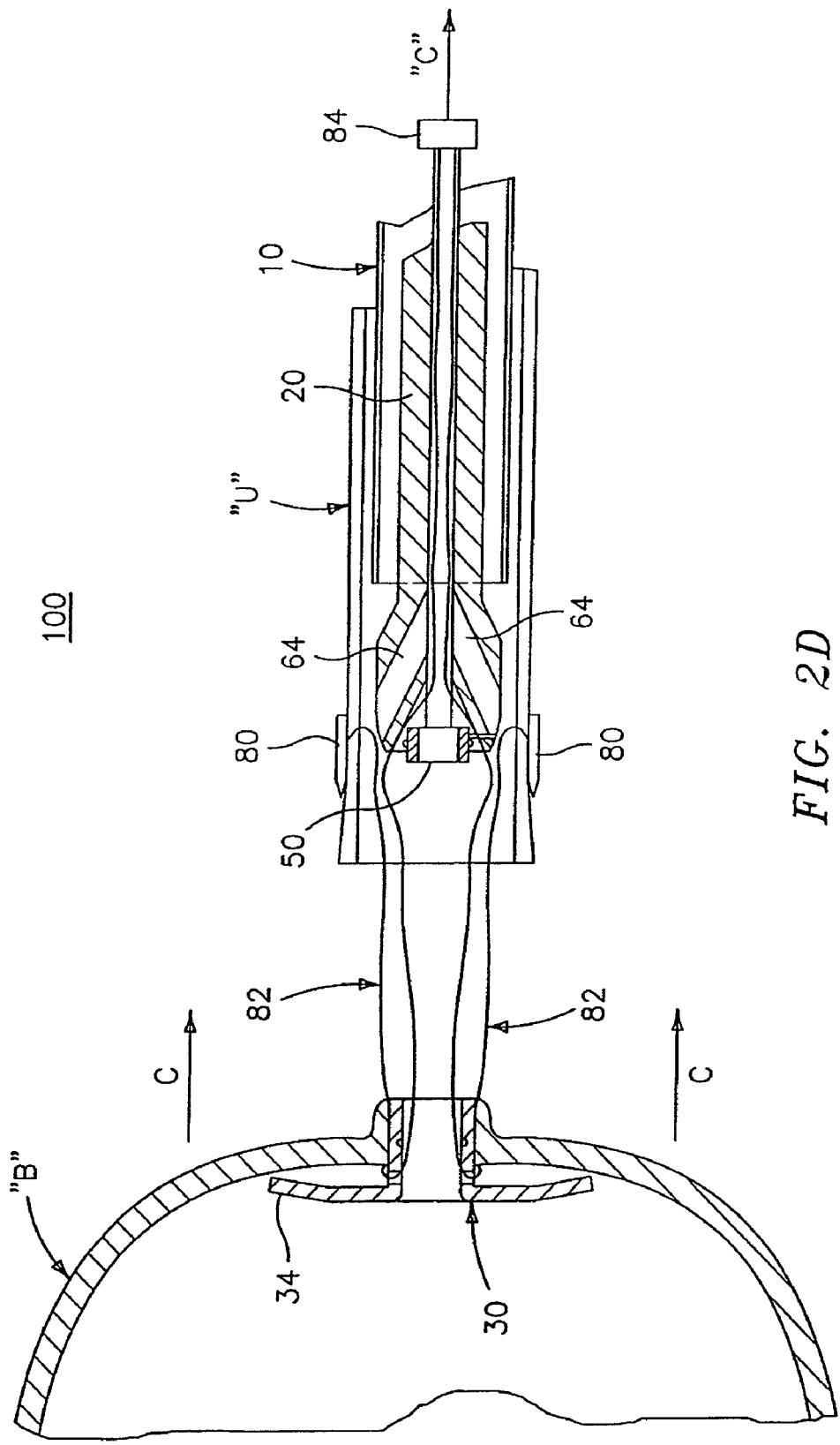
FIG. 2D is a cross-sectional side elevational view of the apparatus as shown in FIG. 1B, with the needle anchors secured to the body lumen.
Figure 2E:
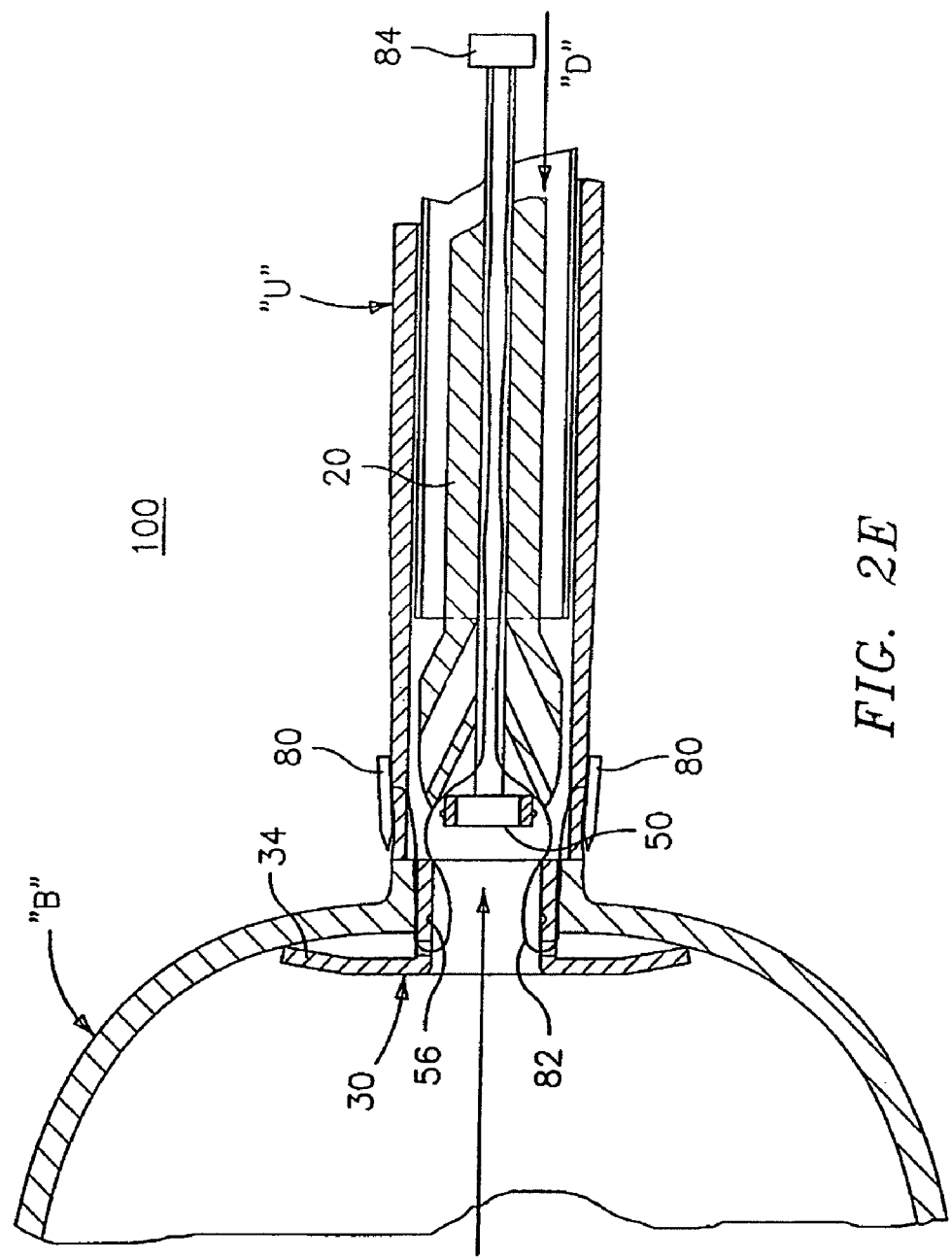
FIG. 2E is a cross-sectional side elevational view of the apparatus as shown in FIG. 1B, illustrating the approximation of the hollow body organ to the body lumen.

In particular, as seen in FIG. 2D, handle 84 is drawn proximally, in a direction "C", thereby pulling on sutures 82. Since needle anchors 80 are secured in place in urethral stump "S" and since expandable anchor 30 is securely held within bladder "B" by arms 34, pulling on or applying tension to sutures 82, in direction "C" will cause sutures 82 extending between urethra "U" and bladder "B" to shorten, thereby approximating bladder neck "N" of bladder "B" to urethral stump "S" of urethra "U". In particular, pulling on handle 84 in direction "C" draws sutures 82 through central lumen 62 of tubular body 20, through recess 66, through passages 58 between lock collar 50 and firing head 60, through central passage 38 of flange 36, through a respective hole 40, between bladder neck "N" and flange 36 and through urethral stump "S" where it is secured to a respective needle anchor 80. Since needle anchors 80 are prevented from coming through urethral stump "S", pulling on handle 84 will cause bladder "B" to be moved in direction "C" and ultimately in the approximation of bladder neck "N" to urethral stump "S", as seen in FIG. 2E.

With bladder neck "N" approximated to urethral stump "S", handle 84 is held, thereby keeping sutures 82 under tension, and tubular body 20 is moved distally in direction "D" (i.e., opposite direction "C"). Tubular body 20 is advanced distally until lock collar 50 is inserted into and/or received in central passage 38 of flange 36. As described above, preferably, lock collar 50 is sized to be tightly fit into flange 36 (i.e., friction fit). More preferably, as described above, tubular body 20 is advanced distally until lock collar 50 is snap fit into flange 36 by the receipt of annular rim 54 into annular channel 56. As seen in FIG. 2F, by having lock collar 50 tightly received in flange 36, the outer surface of lock collar 50 presses against the inner surface of flange 36 thereby squeezing sutures 82 therebetween. In so doing, sutures 82 are prevented from being distally passed through flange 36 which would in turn cause bladder "B" to separate from urethra "U".

With lock collar 50 secured in flange 36, it is envisioned that tubular body 20 is twisted, thereby breaking break-away tabs 52 in order to separate lock collar 50 from tubular body 20. Tubular body 20 is then withdrawn from sleeve 10. As seen in FIG. 2F, sutures 82 are then cut and sleeve 10 withdrawn from urethra "U".

It is contemplated that additional clips, staples, sutures and/or other fastening devices may or may not be used to join urethra "U" and bladder "B" together.

Figure 3A:
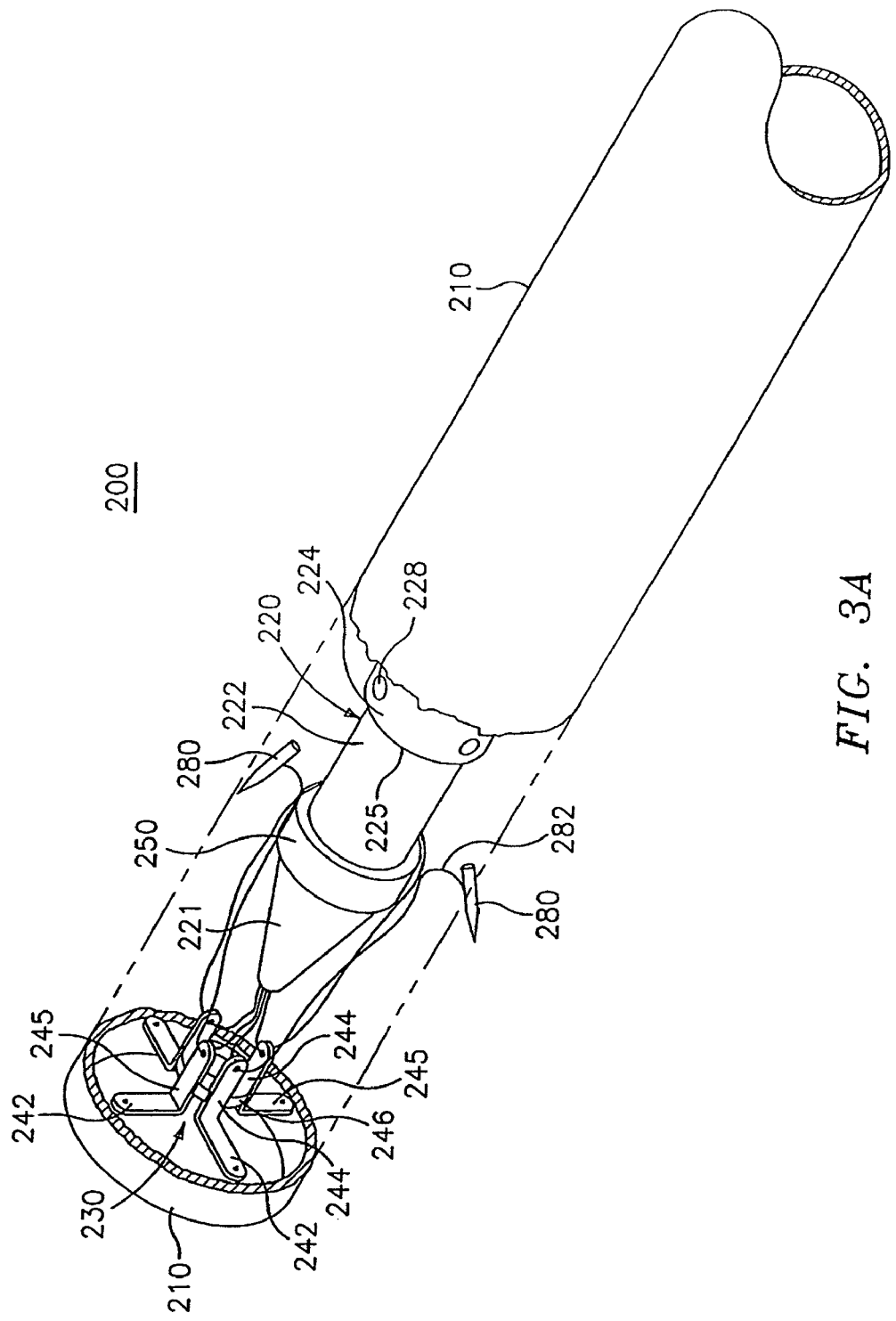
FIG. 3A is a perspective view of a distal end view of another embodiment of an anastomosis apparatus in accordance with the present disclosure.
Figure 3B:
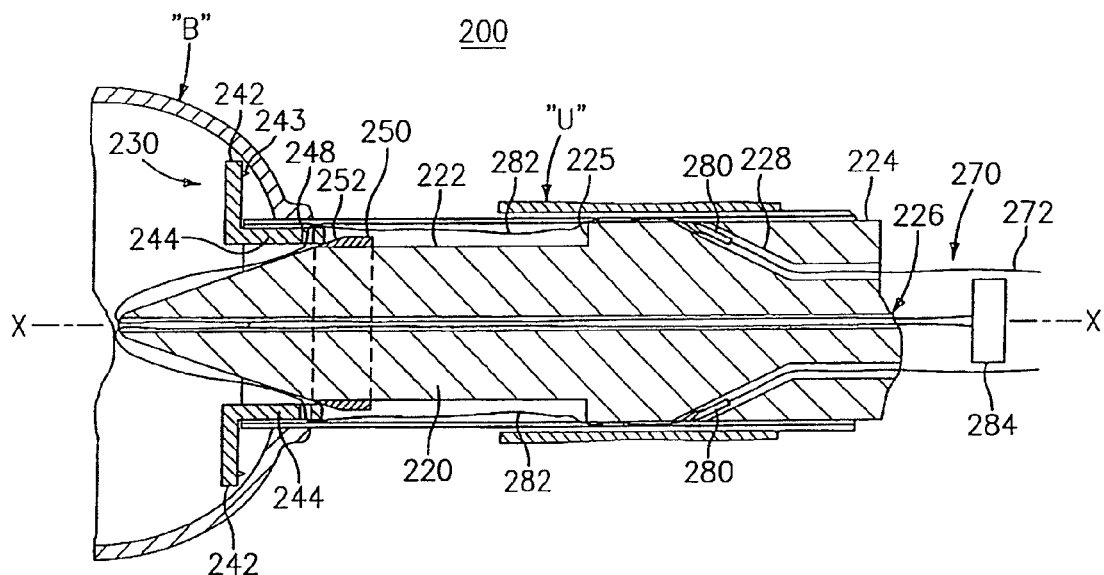
FIG. 3B is a cross-sectional side elevational view showing the apparatus of FIG. 3A, inserted through a body lumen and into a body organ.
Figure 3C:
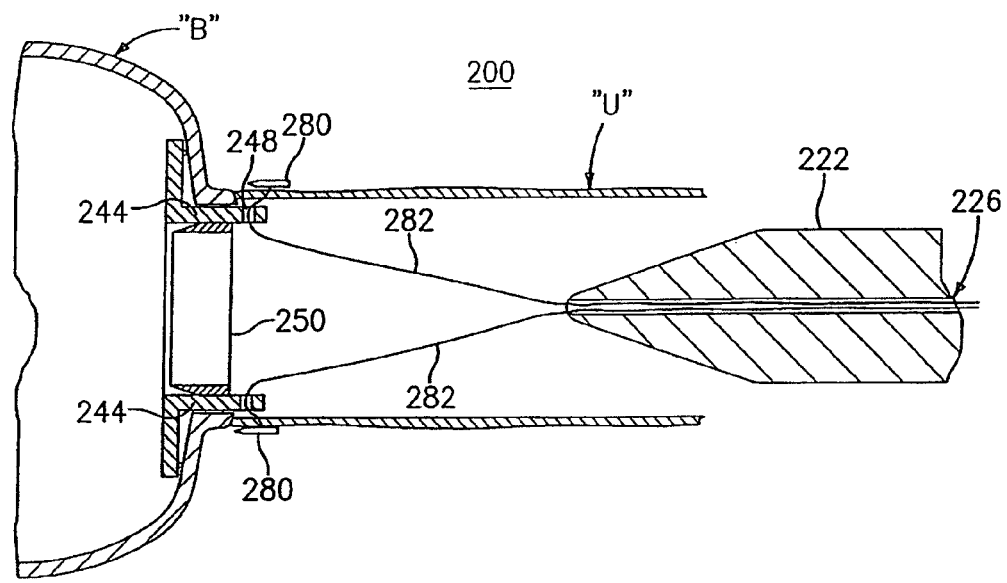
FIG. 3C is a cross-sectional side elevational view showing the apparatus of FIG. 3A, with the body organ approximated to the body lumen.

Referring now to FIGS. 3A-3C, another embodiment of an anastomosis apparatus, in accordance with the present disclosure, is shown generally as 200. Anastomosis apparatus 200 includes an outer sleeve 210, an inner tubular body 220, a detachable or repositionable expandable anchor 230, a lock ring 250 and needle anchors 280.

Inner tubular body 220 is slidably received within outer sleeve 210. Inner tubular body 220 has a distal end portion 222 having a first diameter and a proximal end portion 224 having a second diameter which is greater than the first diameter thereby defining a shoulder 225. Inner tubular body 220 includes a central lumen 226 extending therethrough defining a longitudinal X-axis. Inner tubular body 220 further includes a plurality of longitudinally running firing channels 228 formed therein. Preferably, firing channels 228 include a distal end oriented radially outward at an angle which is obtuse to the longitudinal X-axis. Distal end portion 222 includes a substantially conical tip 221.

Expandable anchor 230 includes a plurality of arms 245 and a lock ring 250. Each arm 245 has a distal portion 242 oriented substantially orthogonal to a longitudinal "X" axis of inner tubular body 220 and a proximal portion 244 oriented substantially linearly with the longitudinal X-axis. Each distal portion 242 includes at least one tooth or spike 243 for engaging the inside wall of the hollow body organ to be joined. Each proximal portion 244 includes at east one hole 248 formed therein.

Arms 245 are preferably arranged such that distal portion 242 of each arm 245 is oriented radially outward. It is envisioned that arms 245 are joined to one another by a break-away member 246 interconnecting each proximal portion 244. In accordance with the present disclosure, expandable anchor 230 has a first position in which proximal portions 244 are in relatively close proximity to one another and interconnected by break-away members 246 and a second position in which proximal portions 244 are relatively further spaced from one another and broken away from at least one break-away member 246. Stated differently, in the first position, proximal portions 244 of expandable anchor 230 are positioned in relatively close proximity to the central longitudinal X-axis and in the second position, proximal portions 244 of expandable anchor 230 are positioned at a relatively further distance to the central longitudinal X-axis.

Preferably, when in the first position, expandable anchor 230 is sized to be received within outer sleeve 210 and when in the second position, distal end portion 242 extends radially beyond outer sleeve 210 and preferably beyond the terminal edge of an opening in a hollow body organ. Preferably, arms 245 are formed of a rigid bio-compatible material, however, it is envisioned that arms 245 can be formed of a resilient bio-compatible material. Arms 245 can also have other shapes, other than L-shaped as shown in FIG. 3A. Anchor 230 is shaped/sized to fit within the opening of bladder "B" in the pre-expanded condition to engage bladder "B" in the expanded condition.

In accordance with the present disclosure, lock ring 250 is slidably positioned on distal end 222 of inner tubular body 220. As best seen in FIG. 3B, lock ring 250 desirably has a substantially trapezoidal radial cross-sectional profile. In particular, lock ring 250 has an angled distal end defining a camming surface 252 and a substantially planar proximal surface configured and adapted to contact shoulder 225 of inner tubular body 220. Lock ring 250 also includes connection features for connecting arms 245 to lock ring 250. For example, lock ring 250 may include grooves sized and shaped to engage and retain arms 245 in a locking fashion and may include a lip for locking arms 245 in lock ring 250. Other features may be used including adhesives.

Desirably, lock ring 250 is releasably attached to body 220 by any known means. For example, a releasable lever on body 220 may be arranged for engagement with the lock ring and releasable by means of a control at a proximal end of the apparatus. Alternatively, a separate tube may be disposed around body 220 for sliding lock ring 250 off of body 220.

Apparatus 200 further includes a plurality of needle anchors 280 slidably received in the distal end of firing channels 228. Each needle anchor 280 is provided with a suture 282 having a first end preferably affixed to a mid-point of a respective needle anchor 280 and a second end affixed to a handle 284. In accordance with the present disclosure, each suture 282 runs from a respective needle anchor 280, distally out of a respective firing channel 228 through hole 248 formed in proximal portion 244 of a respective arm 245, into a distal end of central lumen 226 formed in inner tubular body 220 and proximally therethrough to handle 284.

Apparatus 200 includes a needle anchor pusher assembly 270. Pusher assembly 270 includes a plurality of push rods 272, preferably operatively coupled to one another, slidably disposed within a respective firing channel 228 of inner tubular body 220. Inner tubular body 220 includes a central lumen 226.

Preferably, expandable anchor 230, lock ring 250, anchor needles 280 and sutures 282 are made from a medical grade bio-absorbable material, such as, for example, polyglycolic acid (PGA) and/or polylactic acid (PLA). It is envisioned that expandable anchor 230, lock ring 250, anchor needles 280 and sutures 282 have sufficient endurance to retain their structural integrity for at least the period required for a natural growth joining of tissue portions for a given anastomotic procedure.

A preferred method of use and operation of anastomosis apparatus 200 in performing a radical prostatectomy anastomosis will now be described in detail with reference to FIGS. 3A-3C. With the prostate removed, bladder neck "N" and urethral stump "S" reconstructed, apparatus 200 is passed trans-urethrally through urethra "U" until the distal end of outer sleeve 210 extends out urethral stump "S" and into bladder "B". In particular, apparatus 200 is positioned such that distal portion 242 of arms 245 are positioned in bladder "B".

As seen in FIG. 3B, sleeve 210 is withdrawn in a proximal direction until distal portion 242 of arms 245 are exposed. Inner tubular body 220 is advanced distally until conical tip 221 contacts proximal portion 244 of arms 245. Inner tubular body 220 is then further advanced distally, inserting lock ring 250 between arms 245 causing break-away members to separate from each individual arm 245 thereby causing proximal portion 244 of arms 245 to displace radially outward due to the camming action between proximal portions 244 of arms 245 and conical tip 221 of inner tubular body 220. Inner tubular body 220 is advanced until proximal portions 244 of arms 245 clear conical tip 221 of inner tubular body and are displaced to a radius substantially equal to the radius of distal end portion 222 of inner tubular body 220. Radial displacement of proximal portions 244 of arms 245 causes reconstructed bladder neck "N" to radially stretch, thus creating a constricting force acting radially inward on proximal portions 244 of arms 245.

It is envisioned that as inner tubular body 220 is advanced distally, arms 245 will cause lock ring 250 to slide proximally along distal end portion 222 of inner tubular body 220. As such, inner tubular body 220 is distally advanced until the proximal end of lock ring 250 is stopped by shoulder 225 of inner tubular body 220. Inner tubular body 220 is further advanced distally causing proximal end portion 224 of arms 245 to be further displaced radially outward due to the camming action between proximal portions 244 of arms 245 and camming surface 252 of lock ring 250. Arms 245 are enlarged by and attached to lock ring 250.

Outer sleeve 210 and inner tubular body 220 are then withdrawn proximally back through urethral "U". Accordingly, distal end portion 222 of inner tubular body 220 is withdrawn from lock ring 250 which lock ring 250 is held in place due to the constricting force of bladder neck "N" pressing into proximal portions 244 of arms 245 which in turn press into lock ring 250.

Outer sleeve 210 and inner tubular body 220 are withdrawn proximally until the distal end of firing channels 228 of inner tubular body 220 is positioned proximally of urethral stump "S". With inner tubular body 220 so positioned, outer sleeve 210 is withdrawn proximally, while inner tubular body 220 is held in place, until the distal end of firing channels 228 are exposed.

Apparatus 200 is then fired by advancing push rods 272 of pusher assembly 270 distally through firing channels 228 thereby forcing needle anchors 280 radially out of firing channels 228. Pusher assembly 270 is distally advanced until needle anchors 280 completely penetrate through urethral stump "S". Push rods 272 are then withdrawn proximally back through firing channels 228.

With needle anchors 280 secured in place, as seen in FIG. 3C, sutures 282 are withdrawn proximally through central lumen 226 of inner tubular body 220 by pulling on handle 284. By pulling on handle 284, sutures 282 are drawn through holes 248 formed in proximal portion 244 of arms 245, thereby approximating bladder "B" to urethra "U". By pulling on sutures 282 proximally through central lumen 226 of inner tubular body 220, teeth 243 of distal portion 242 of arms 245 digs into the inner surface of bladder "B" thereby further securing expandable anchor 230 into position. Sutures 282 are then cut and secured in place in order to prevent bladder "B" from separating from urethra "U".

The sutures may be secured as disclosed in commonly assigned U.S. Application entitled "Method and Apparatus for Radical Prostatectomy Anastomosis Including and Anchor for Engaging a Body Vessel and Deployable Needles", filed on even date herewith, the disclosure of which is hereby incorporated by reference herein, in its entirety.

Figure 4A:
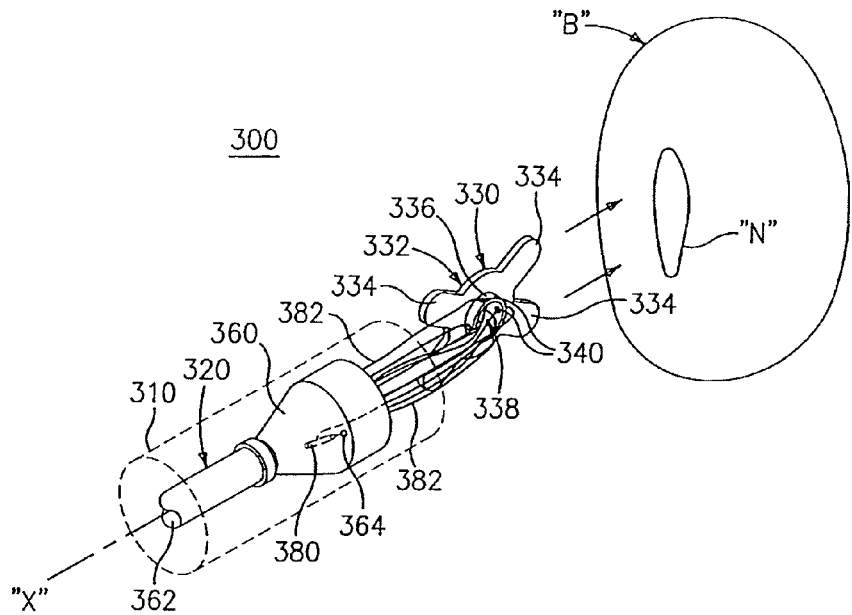
FIG. 4A is a perspective view of a distal end view of an additional embodiment of the anastomosis apparatus, in accordance with the present disclosure, inserted through a body lumen.
Figure 4B:
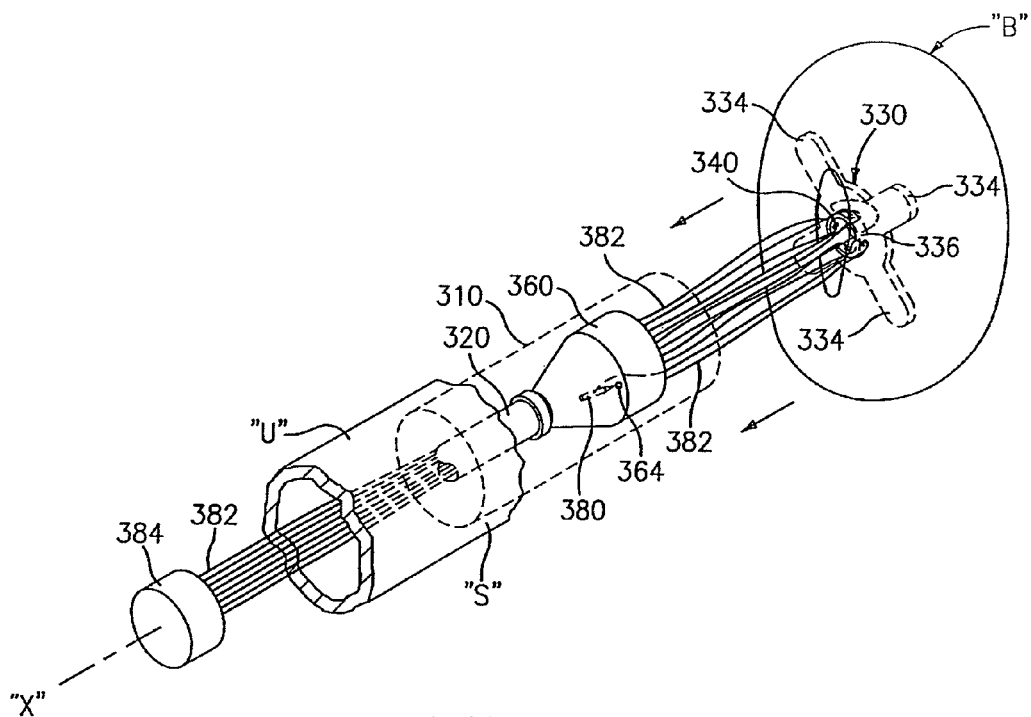
FIG. 4B is a perspective view of the apparatus shown in FIG. 4A illustrating the approximation of the body lumen with a body organ.

Turning now to FIGS. 4A-4B, another embodiment of an anastomosis apparatus, in accordance with the present disclosure, is shown generally as 300. Apparatus 300 includes a sleeve 310 and a tubular body 320 slidably received within sleeve 310. Sleeve 310 and tubular body 320 of apparatus 300 are substantially similar to sleeve 10, tubular body 20 of apparatus 100 disclosed above. Accordingly, the detailed description of sleeve 10 and tubular body 20 of apparatus 100 from above will act as the detailed description for sleeve 310 and tubular body 320 of apparatus 300.

In accordance with the present embodiment and as seen in FIGS. 4A and 4B, apparatus 300 further includes an anchor 330. Anchor 330 includes a plate 332, a plurality of arms 334 extending radially outward from plate 332 and an annular flange 336 extending from a proximal surface of plate 332. Preferably, a plurality of arms 334 is desired and more preferably, two pair of equally spaced diametrically opposed arms 334 is desired. In accordance with the present embodiment, it is preferred that arms 334 are semi-rigid and/or substantially rigid. In this manner, it is contemplated that arms 334 will not deflect or deform and will substantially maintain their configuration when exposed to deforming forces. It is further envisioned that anchor 330 is dimensioned such that anchor 330 can be received within sleeve 320.

In addition, plate 332 and flange 336 define a central passage 338 extending completely therethrough. Flange 336 includes a plurality of holes 340 formed radially therethrough.

Apparatus 300 further includes a plurality of needle anchors 380 slidably received within a respective needle passage 364 of a firing head 360 on tubular body 320. Each needle anchor 380 is provided with a suture 382 having a first end affixed to a mid-point of a respective needle anchor and a second end affixed to a common handle 384. In accordance with the present disclosure, each suture 382 runs from a respective needle anchor 380, distally out of a respective needle passage 364, into central passage 338 of flange 336 via a respective hole 340, proximally into a firing head 360 and proximally through a central lumen 362 formed in tubular body 320 to handle 384.

Preferably, anchor 330, anchor needles 380 and sutures 382 are made from a medical grade bio-absorbable material, such as, for example, polyglycolic acid (PGA) and/or polylactic acid (PLA). It is envisioned that anchor 330, anchor needles 380 and sutures 382 have sufficient endurance to retain their structural integrity for at least the period required for a natural growth joining of tissue portions for a given anastomotic procedure.

A preferred method of use and operation of anastomosis apparatus 300, in performing a radical prostatectomy anastomosis, will now be described in greater detail with reference to FIGS. 4A and 4B. With the prostate removed, bladder neck "N" and urethral stump "S" reconstructed, apparatus 300 is passed trans-urethrally through urethra "U" until the distal end of outer sleeve 310 extends out urethral stump "S".

In particular, as seen in FIG. 4A, anchor 330 is then removed from the distal end of outer sleeve 310 and rotated such that a center line passing through central passage 338 of anchor 330 is substantially orthogonal to the longitudinal X-axis. For example, anchor 330 may be engaged by a surgical device, such as a grasper and rotated by the surgeon. Anchor 330 is then entirely slipped into bladder "B" through bladder neck "N" in the manner of a button/button-hole arrangement. As seen in FIG. 4B, once inserted into bladder "B", anchor 330 is rotated in order to substantially align the center line passing through central passage 338 of anchor 330 with the longitudinal X-axis. In so doing, arms 334 of anchor 330 extend across bladder neck "N" and beyond the terminal edge of bladder neck "N", thereby preventing anchor 330 from being removed from or pulled out of bladder "B".

With anchor 330 in position in bladder "B", apparatus 300, including sleeve 310 and tubular body 320, is withdrawn proximally through urethra "U" until needle passages 364 are within urethra "U". With needle passages 364 exposed, apparatus 300 is fired by advancing needle push rods (not shown) through tubular body 320 until needle anchors 380 are pushed through the walls of urethral "U". With needle anchors 380 secured to urethra "U", the needle push rods are then withdrawn from apparatus 300.

With needle anchors 380 secured to urethra "U", handle 384 is drawn proximally to thereby pull on and tighten sutures 382. By pulling proximally on handle 384, bladder "B" brought into approximation with urethra "U". Sutures 282 are then cut and secured in place in order to prevent bladder "B" from separating from urethra "U".

Although the illustrative embodiments of the present disclosure have been described herein with reference to the accompanying drawings, it is to be understood that the disclosure is not limited to these embodiments, and that various other changes and modifications may be affected therein by one skilled in the art without departing from the scope or spirit of the disclosure. For example, some or all of the sutures, needle anchors, and expandable anchor are formed from bioabsorbable material or materials. In addition, the needle anchors may have other shapes, such as hook-shaped, or any other shape. All such changes and modifications are intended to be included within the scope of the appended claims.

What is claimed is:

1. A device for joining a first body vessel to a second body vessel, comprising:
   a) a cartridge having a distal end and defining a longitudinal axis, wherein the cartridge comprises an inner member and an outer member having a lumen dimensioned to receive the inner member;
   b) a radially expandable anchor disposed at the distal end of the cartridge for engaging the first body vessel, wherein the expandable anchor includes a plurality of arms having an initial condition and an expanded condition, and wherein the inner member includes a ring having connection features for engaging the expandable anchor;
   c) a plurality of sutures disposed within the cartridge and being deployable therefrom so as to engage the second body vessel, the sutures being disposed in channels formed in the inner member and threaded through the expandable anchor;
   d) a plurality of needle anchors, wherein at least one of the needle anchors is attached to a distal end of a respective suture; and
   e) a ring for securing the sutures to the expandable anchor.

2. The device according to claim 1, wherein the expandable anchor has a plurality of arms connected by members.

3. The device according to claim 2, wherein the ring, expandable anchor, and members are sized and arranged so that when the ring engages the arms, the members are broken.

4. The device according to claim 1, wherein the plurality of arms are biased toward an expanded position.

5. The device according to claim 1, wherein the expandable anchor has a central passage and the sutures extend through the expandable anchor and proximally through the central passage.

6. The device according to claim 1, wherein the expandable anchor is disposed between the inner member and the outer member.

7. The device according to claim 1, wherein the expandable anchor is deployable from the cartridge.

8. The device according to claim 1, wherein the inner member has a tapered distal end.

* * * * *